United States Patent [19]

Rentzea et al.

[11] 4,385,925
[45] May 31, 1983

[54] 1,3-DIOXAN-5-YL-ALKYLTRIAZOLES, THEIR PREPARATION, THEIR USE FOR REGULATING PLANT GROWTH, AND REGULATORS CONTAINING THESE COMPOUNDS

[75] Inventors: Costin Rentzea, Heidelberg; Karl-Heinz Feuerherd; Bernd Zeeh, both of Ludwigshafen; Johann Jung, Limburgerhof, all of Fed. Rep. of Germany

[73] Assignee: BASF Aktiengesellschaft, Fed. Rep. of Germany

[21] Appl. No.: 279,584

[22] Filed: Jul. 1, 1981

[30] Foreign Application Priority Data

Jul. 9, 1980 [DE] Fed. Rep. of Germany ....... 3025879

[51] Int. Cl.³ .................. A01N 43/64; C07D 405/06; C07D 405/14; C07D 409/14
[52] U.S. Cl. .......................................... 71/92; 71/76; 71/90; 71/78; 549/372; 548/262; 549/60; 549/370
[58] Field of Search ..................... 548/262; 71/76, 78, 71/92, 90

[56] References Cited

U.S. PATENT DOCUMENTS 3,156,554 11/1964 Tolbert .................................. 71/2.7
4,259,505 3/1981 Sturm et al. ........................ 548/336
4,289,526 9/1981 Worthington et al. ............. 424/269

FOREIGN PATENT DOCUMENTS 2739352 3/1979 Fed. Rep. of Germany ...... 548/262

Primary Examiner—Alton D. Rollins
Attorney, Agent, or Firm—Keil & Witherspoon

[57] ABSTRACT

Compounds of the formula

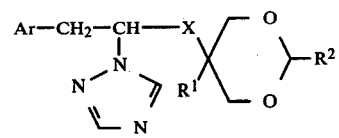

where Ar, $R^1$, $R^2$ and X have the meanings given in the claims, their preparation and their use as plant growth regulators.

5 Claims, No Drawings

1,3-DIOXAN-5-YL-ALKYLTRIAZOLES, THEIR PREPARATION, THEIR USE FOR REGULATING PLANT GROWTH, AND REGULATORS CONTAINING THESE COMPOUNDS

The present invention relates to novel 1,3-dioxan-5-yl-alkyltriazoles, processes for their preparation, plant growth regulators which contain these compounds, and processes for regulating plant growth, using these compounds.

It is known that certain 2-haloethyl-trialkylammonium halides have plant growth-regulating properties (cf. U.S. Pat. No. 3,156,554). Thus, plant growth can be influenced with the aid of 2-chloroethyl-trimethylammonium chloride. However, the activity of this compound is not always adequate, especially if low amounts are used.

Further, German Laid-Open Application DOS No. 2,739,352 has disclosed the use of 3,3-dimethyl-2-(1,2,4-triazol-1-yl)-1-(4-chlorobenzoyl)-butane for regulating plant growth.

We have found that compounds of the formula I

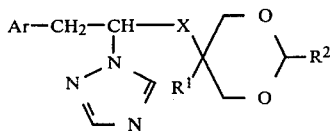

where $R^1$ and $R^2$ are identical or different and each is hydrogen or alkyl of 1 to 5 carbon atoms, Ar is furanyl, thienyl, biphenylyl or naphthyl, or is phenyl which is unsubstituted or substituted by fluorine, chlorine, bromine, iodine, nitro or trifluoromethyl, or by alkyl, alkoxy or alkenyl, each of 1 to 5 carbon atoms, or by phenoxy, and X is —CO—, —CH(OH)— or —CH(OR$^3$)—, where $R^3$ is unsubstituted or chlorine substituted alkyl of 1 to 8 carbon atoms or unsubstituted or chlorine-substituted alkenyl of 2 to 5 carbon atoms, or alkynyl of 3 or 4 carbon atoms or benzyl which is unsubstituted or substituted by fluorine, chlorine, bromine, nitro or trifluoromethyl or by alkyl or alkoxy of 1 to 4 carbon atoms, or $R^3$ is —CO—R$^4$, where $R^4$ is alkyl of 1 to 5 carbon atoms which is unsubstituted or substituted by halogen, alkenyl of 2 to 5 carbon atoms, alkoxy, oxo (=O) or carboxyalkyl or is an aromatic radical, are outstandingly useful for influencing the growth of plants and are very well tolerated by them.

The novel compounds of the formula I contain chiral centers and are in general obtained in the form of racemates or as diastereomer mixtures of erythro-forms and threo-forms. The erythro-diastereomers and threo-diastereomers can, in the case of some of the compounds according to the invention, be separated by, for example, utilizing solubility differences or employing column chromatography, and can thus be isolated in a pure form. Individual enantiomers can be obtained from such individual pairs of diastereomers by conventional methods and are also a subject of the present invention. Either the individual diastereomers or enantiomers, or the mixtures resulting from the synthesis process, can be used as agents for influencing plant growth. Preferably, the mixtures are employed.

$R^1$ and $R^2$ are, for example, hydrogen, methyl, ethyl, n-propyl, isopropyl, n-butyl, sec.-butyl, isobutyl, tert.-butyl, n-pentyl or neopentyl.

Ar is, for example, furan-2-yl, thien-2-yl, thien-3-yl, biphenyl-4-yl, naphth-1-yl, naphth-2-yl, phenyl, 4-fluorophenyl, 2-chlorophenyl, 3-chlorophenyl, 4-chlorophenyl, 4-bromophenyl, 2,4-dichlorophenyl, 3,4-dichlorophenyl, 3,5-dichloro-2-methoxyphenyl, 2,3,4-trichlorophenyl, 2-methoxyphenyl, 2,4-dimethoxyphenyl, 3-methoxyphenyl, 4-methoxyphenyl, 4-ethoxyphenyl, 4-tert.-butoxyphenyl, 4-methylphenyl, 4-ethylphenyl, 4-isopropylphenyl, 4-tert.-butylphenyl, 3-nitrophenyl, 4-nitrophenyl, 3-trifluoromethylphenyl, 4-trifluoromethylphenyl and 4-phenoxyphenyl.

X is, for example, carbonyl (C=O) or an alcohol group (—CHOH) resulting therefrom by reduction; the alcohol group can also be etherified (to —CH—OR$^3$) or esterified (to —CH—OCOR$^4$), where $R^3$ is, for example, methyl, ethyl, n-propyl, n-butyl, 4-chlorobutyl, n-pentyl, n-hexyl, allyl, buten-2-yl, propargyl, benzyl, 4-fluorobenzyl, 4-chlorobenzyl, 4-bromobenzyl, 2,4-dichlorobenzyl or 4-trifluoromethylbenzyl and $R^4$ is preferably methyl, ethyl, n-propyl, isopropyl, chloromethyl, chloropropyl, methoxymethyl, vinyl or propenyl.

The novel compounds are obtained when (a) a 1,2,4-triazole is reacted with an α-bromoketone of the formula II

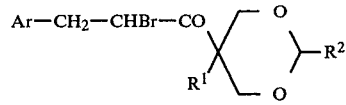

where $R^1$, $R^2$ and Ar have the above meanings, or (b) an arylmethyl halide of the formula III

AR—CH$_2$—Y    III where Ar has the above meanings and Y is chlorine or bromine, is reacted with a 1-(1,3-dioxan-5-yl)-2-(1,2,4-triazolyl-(s))-ethan-1-one of the formula IV

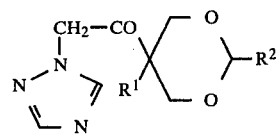

where $R^1$ and $R^2$ have the above meanings, with or without subsequent reduction of the compound obtained, the reduction being followed, if desired, by etherification or esterification.

Reaction (a) is carried out in the presence or absence of a solvent or diluent, with or without addition of an inorganic or organic base, and with or without addition of a reaction accelerator, at from 10° to 120° C. The preferred solvents and diluents include ketones, eg. acetone, methyl ethyl ketone and cyclohexanone, nitriles, eg. acetonitrile, esters, eg. ethyl acetate, ethers, eg. diethyl ether, tetrahydrofuran or dioxane, sulfoxides, eg. dimethylsulfoxide, amides, eg. dimethylformamide, dimethylacetamide and N-methylpyrrolidone, sulfolan and mixtures of the above.

Examples of suitable bases, which can, where appropriate, also be used as acid acceptors in the reaction, are alkali metal hydroxides, eg. lithium hydroxide, sodium hydroxide or potassium hydroxide, alkali metal carbonates, eg. sodium carbonate, potassium carbonate, sodium bicarbonate and potassium bicarbonate, or an excess of 1,2,4-triazole, pyridine or 4-dimethylaminopyridine. (Translator's note: we understand the reference to an excess of 1,2,4-triazole, as this is one of the reactants in method (a), but are baffled by the reference to excess pyridine or excess 4-dimethylaminopyridine since these have no part in the reaction). Other conventional bases may, however, also be employed.

Preferred reaction accelerators are metal halides, eg. sodium iodide and potassium iodide, quaternary ammonium salts, eg. tetrabutylammonium chloride, bromide and iodide and benzyltriethylammonium chloride and bromide, and crown ethers, eg. 12-crown-4, 15-crown-5, 18-crown-6, dibenzo-18-crown-6 and dicyclohexano-18-crown-6.

The reactions are in general carried out at from 20° to 150° C., under atmospheric or superatmospheric pressure, continuously or batchwise.

The bromoketones of the formula II are novel compounds. They can be prepared, for example, by brominating a compound of the formula V

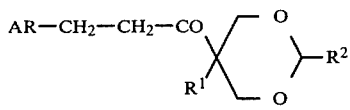

where Ar, $R^1$ and $R^2$ have the above meanings, with bromine in formamide, using the method of H. Bredereck et al., Chem. Ber. 93, (1960), 2083, or with dioxane-dibromide by the method of S. J. Pasaribu and L. R. Williams, Aust. J. Chem. 26, (1973), 1327, or with the (pyrrolidone)$_3$.HBr.Br$_2$ complex, by the method of D. C. Awang et al., Can. J. Chem. 47, (1969), 706.

Reaction (b) is carried out in the presence or absence of a solvent or diluent and with or without addition of a strong inorganic or organic base, at from −10° to 120° C. The preferred solvents ad diluents include amides, eg. dimethylformamide, diethylformamide, dimethylacetamide, diethylacetamide, N-methylpyrrolidone and hexamethylphosphorotriamide, sulfoxides, eg. dimethylsulfoxide, and also sulfolan.

Suitable bases, which where appropriate, can also be used as acid acceptors in the reaction, are, for example, alkali metal hydrides, such as lithium hydride, sodium hydride and potassium hydride, alkali metal amides, such as sodium amide and potassium amide, sodium tert.-butoxide, potassium tert.-butoxide, lithium-triphenylmethyl, sodium-triphenylmethyl, potassium-triphenylmethyl, naphthalene-lithium, naphthalene-sodium and naphthalene-potassium.

The 1-(1,3-dioxan-5-yl)-2-(1,2,4-triazol-1-yl)-ethan-1-ones of the formula IV are novel compounds. They can be prepared, for example, by reacting a 2-halo-1-(2,5-dialkyl-1,3-dioxan-5-yl)-ethan-1-one of the formula VI

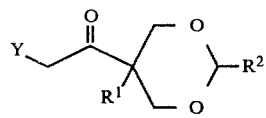

where $R^1$, $R^2$ and Y have the above meanings, with 1,2,4-triazole or an alkali metal salt thereof, in a suitable solvent.

The haloketones of the formula VI are also novel compounds. They are obtained, for example, by brominating a known (1,3-dioxan-5-yl)-ethan-1-one of the formula VII

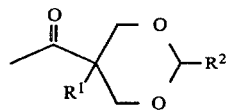

where $R^1$ and $R^2$ have the above meanings, for example with the pyrrolidone-bromine complex, using the method of D. P. Wyman and P. R. Kaufman, J. Org. Chem. 29, (1964), 1956.

Ketones obtained according to (a) or (b) can, if desired, be reduced, in the presence or absence of a solvent or diluent, at from −20° to 150° C., under atmospheric pressure or superatmospheric pressure, by means of hydrogen in the presence of a catalyst, or by complex boron hydrides or aluminum hydrides, by aluminum isopropoxide in isopropanol, by sodium dithionite or electrochemically.

Examples of suitable solvents or diluents for the reductions are water, methanol, ethanol, isopropanol, acetic acid, diethyl ether, tetrahydrofuran, dioxane, ethyl acetate, toluene, dimethylformamide or mixtures of these.

The catalytic hydrogenation is carried out in the presence of a platinum catalyst or palladium catalyst on an inert carrier, under a pressure of from 2 to 80 bar, until hydrogen ceases to be taken up.

Examples of the hydrides which can be used as reducing agents are sodium borohydride and lithium aluminum hydride.

A resulting alcohol, of the formula I (X=CHOH) can be etherified with an alkylating agent of the formula VIII $$Z-R^3 \qquad \text{VIII}$$

where $R^3$ has the above meanings and Z is chlorine or bromine, in the presence or absence of a solvent or diluent which forms a one-phase or two-phase system, with or without addition of an inorganic base and with or without addition of a reaction accelerator and/or phase transfer catalyst.

Suitable solvents or diluents are diethyl ether, tetrahydrofuran, dioxane, n-pentane, monohalohydrocarbons of 2 to 6 carbon atoms, eg. chloroethane, bromoethane, 1-chloropropane, 1-bromopropane, 1-chlorobutane, 1-bromobutane, 1-chloropentane, 1-bromopentane, 1-chlorohexane and 1-bromohexane, as well as cyclohexane, methylene chloride, chloroform, toluene and dimethylformamide.

Examples of suitable inorganic bases are alkali metal hydroxides and alkaline earth metal hydroxides, eg. sodium hydroxide, potassium hydroxide, calcium hydroxide and barium hydroxide, alkali metal carbonates and alkaline earth metal carbonates, eg. sodium carbonate, potassium carbonate, sodium bicarbonate, potassium bicarbonate, calcium carbonate and barium carbonate, and alkali metal alcoholates and alkaline earth metal alcoholates, eg. sodium methylate, sodium ethylate, magnesium methylate, sodium isopropylate and potassium tert.-butylate.

Examples of suitable reaction accelerators are metal halides, eg. sodium bromide, sodium iodide, potassium bromide and potassium iodide, tertiary amines, eg. 4-dimethylaminopyridine and 4-pyrrolidinopyridine, crown ethers, eg. 12-crown-4, 14-crown-5, 18-crown-6, dibenzo-18-crown-6 and dicyclohexano-18-crown-6, and azoles, eg. imidazole and 1,2,4-triazole.

Preferred phase transfer catalysts are quaternary ammonium salts, such as tetrabutylammonium chloride, bromide, iodide and bisulfate, benzyltriethylammonium chloride and methyltrioctylammonium chloride and bromide, and phosphonium salts, eg. tetrabutylphosphonium bromide and iodide and tetra-n-pentylphosphonium bromide and iodide.

The esterification of the alcohols of the formula I (X=CHOH) can be effected with an acid chloride or acid anhydride of the respective formulae Y—CO—$R^4$ (IX) or ($R^4$—CO)$_2$O (X), in the presence or absence of a solvent or diluent, with or without addition of an acid acceptor and with or without addition of a reaction accelerator. Suitable solvents and bases include those mentioned for the etherification; in addition, tertiary amines, eg. trimethylamine, triethylamine, N,N-dimethylaniline, N,N-dimethylcyclohexylamine, N-methylpiperidine and pyridine, can be used as the base.

Using suitable bases, for example an alkali metal hydride, such as sodium hydride, or an alkali metal alcoholate or alkaline earth metal alcoholate, such as sodium methylate, it is also possible first to convert the alcohols to their alcoholate salts and then to react them in this form.

The resulting compounds of the formula I are isolated by conventional methods, purified if necessary, and if desired, converted to salts or metal complexes by reaction with acids or metal salts respectively.

Specific examples of the novel compounds according to the invention, of the formula I, are 1-(5-methyl-1,3-dioxan-5-yl)-2-(1,2,4-triazol-1-yl)-3-phenyl-propan-1-one, 1-(5-methyl-1,3-dioxan-5-yl)-2-(1,2,4-triazol-1-yl)-3-phenyl-propan-1-ol, 1-(5-methyl-1,3-dioxan-5-yl)-1-methoxy-2-(1,2,4-triazol-1-yl)-3-phenyl-propane, 1-(5-methyl-1,3-dioxan-5-yl)-1-ethoxy-2-(1,2,4-triazol-1-yl)-3-phenyl-propane, 1-(5-methyl-1,3-dioxan-5-yl)-1-propoxy-2-(1,2,4-triazol-1-yl)-3-phenyl-propane, 1-(5-methyl-1,3-dioxan-5-yl)-1-n-butoxy-2-(1,2,4-triazol-1-yl)-3-phenyl-propane, 1-(5-methyl-1,3-dioxan-5-yl)-1-n-pentoxy-2-(1,2,4-triazol-1-yl)-3-phenyl-propane, 1-(5-methyl-1,3-dioxan-5-yl)-1-allyloxy-2-(1,2,4-triazol-1-yl)-3-phenyl-propane, 1-(5-methyl-1,3-dioxan-5-yl)-1-propargyloxy-2-(1,2,4-triazol-1-yl)-3-phenyl-propane, 1-(5-methyl-1,3-dioxan-5-yl)-1-acetoxy-2-(1,2,4-triazol-1-yl)-3-phenyl-propane, 1-(5-methyl-1,3-dioxan-5-yl)-1-propionyloxy-2-(1,2,4-triazol-1-yl)-3-phenyl-propane, 1-(2-ethyl-5-methyl-1,3-dioxan-5-yl)-2-(1,2,4-triazol-1-yl)-3-phenyl-propan-1-one, 1-(2-ethyl-5-methyl-1,3-dioxan-5-yl)-2-(1,2,4-triazol-1-yl)-3-phenyl-propan-1-ol, 1-(5-methyl-1,3-dioxan-5-yl)-2-(1,2,4-triazol-1-yl)-3-(naphth-1-yl)-propan-1-one, 1-(5-methyl-1,3-dioxan-5-yl)-2-(1,2,4-triazol-1-yl)-3-(naphth-1-yl)-propan-1-ol, 1-(5-methyl-1,3-dioxan-5-yl)-1-methoxy-2-(1,2,4-triazol-1-yl)-3-(naphth-1-yl)-propane, 1-(5-methyl-1,3-dioxan-5-yl)-1-n-propoxy-2-(1,2,4-triazol-1-yl)-3-(naphth-1-yl)-propane, 1-(5-methyl-1,3-dioxan-5-yl)-1-n-butoxy-2-(1,2,4-triazol-1-yl)-3-(naphth-1-yl)-propane, 1-(5-methyl-1,3-dioxan-5-yl)-1-allyloxy-2-(1,2,4-triazol-1-yl)-3-(naphth-1-yl)-propane, 1-(5-methyl-1,3-dioxan-5-yl)-1-acetoxy-2-(1,2,4-triazol-1-yl)-3-(naphth-1-yl)-propane, 1-(5-methyl-1,3-dioxan-5-yl)-1-(chloroacetoxy)-2-(1,2,4-triazol-1-yl)-3-(naphth-1-yl)-propane, 1-(5-methyl-1,3-dioxan-5-yl)-1-propionyloxy-2-(1,2,4-triazol-1-yl)-3-(naphth-1-yl)-propane, 1-(2-ethyl-5-methyl-1,3-dioxan-5-yl)-2-(1,2,4-triazol-1-yl)-3-(naphth-1-yl)-propan-1-one, 1-(2-ethyl-5-methyl-1,3-dioxan-5-yl)-2-(1,2,4-triazol-1-yl)-3-naphth-1-yl)-propan-1-ol, 1-(2-propyl-5-methyl-1,3-dioxan-5-yl)-2-(1,2,4-triazol-1-yl)-3-(naphth-1-yl)-propan-1-one, 1-(2-ethyl-5-methyl-1,3-dioxan-5-yl)-1-acetoxy-2-(1,2,4-triazol-1-yl)-3-(naphth-1-yl)-propane, 1-(5-methyl-1,3-dioxan-5-yl)-2-(1,2,4-triazol-1-yl)-3-(4-fluorophenyl)-propan-1-one, 1-(5-methyl-1,3-dioxan-5-yl)-2-(1,2,4-triazol-1-yl)-3-(4-fluorophenyl)-propan-1-ol, 1-(5-methyl-1,3-dioxan-5-yl)-1-n-propoxy-2-(1,2,4-triazol-1-yl)-3-(4-fluorophenyl)-propane, 1-(5-methyl-1,3-dioxan-5-yl)-1-acetoxy-2-(1,2,4-triazol-1-yl)-3-(4-fluorophenyl)-propane, 1-(2-ethyl-5-methyl-1,3-dioxan-5-yl)-2-(1,2,4-triazol-1-yl)-3-(4-fluorophenyl)-propan-1-one, 1-(2-ethyl-5-methyl-1,3-dioxan-5-yl)-2-(1,2,4-triazol-1-yl)-3-(4-fluorophenyl)-propan-1-ol, 1-(5-methyl-1,3-dioxan-5-yl)-2-(1,2,4-triazol-1-yl)-3-(4-chlorophenyl)-propan-1-one, 1-(5-methyl-1,3-dioxan-5-yl)-2-(1,2,4-triazol-1-yl)-3-(4-chlorophenyl)-propan-1-ol, 1-(2,5-dimethyl-1,3-dioxan-5-yl)-2-(1,2,4-triazol-1-yl)-3-(4-chlorophenyl)-propan-1-one, 1-(2,5-dimethyl-1,3-dioxan-5-yl)-2-(1,2,4-triazol-1-yl)-3-(4-chlorophenyl)-propan-1-ol, 1-(2-ethyl-5-methyl-1,3-dioxan-5-yl)-2-(1,2,4-triazol-1-yl)-3-(4-chlorophenyl)-propan-1-one, 1-(2-ethyl-5-methyl-1,3-dioxan-5-yl)-2-(1,2,4-triazol-1-yl)-3-(4-chlorophenyl)-propan-1-ol, 1-(2-n-propyl-5-methyl-1,3-dioxan-5-yl)-2-(1,2,4-triazol-1-yl)-3-(4-chlorophenyl)-propan-1-one, 1-(2-n-propyl-5-methyl-1,3-dioxan-5-yl)-2-(1,2,4-triazol-1-yl)-3-(4-chlorophenyl)-propan-1-ol, 1-(2-isopropyl-5-methyl-1,3-dioxan-5-yl)-2-(1,2,4-triazol-1-yl)-3-(4-chlorophenyl)-propan-1-one, 1-(2-isopropyl-5-methyl-1,3-dioxan-5-yl)-2-(1,2,4-triazol-1-yl)-3-(4-chlorophenyl)-propan-1-ol, 1-(2-n-butyl-5-methyl-1,3-dioxan-5-yl)-2-(1,2,4-triazol-1-yl)-3-(4-chlorophenyl)-propan-1-one, 1-(2-n-butyl-5-methyl-1,3-dioxan-5-yl)-2-(1,2,4-triazol-1-yl)-3-(4-chlorophenyl)-propan-1-ol, 1-(5-methyl-1,3-dioxan-5-yl)-1-methoxy-2-(1,2,4-triazol-1-yl)-3-(4-chlorophenyl)-propane, 1-(5-methyl-1,3-dioxan-5-yl)-1-(but-2-enoyloxy)-2-(1,2,4-triazol-1-yl)-3-(4-chlorophenyl)-propane, 1-(5-methyl-1,3-dioxan-5-yl)-1-n-propoxy-2-(1,2,4-triazol-1-yl)-3-(4-chlorophenyl)-propane, 1-(5-methyl-1,3-dioxan-5-yl)-1-n-butoxy-2-(1,2,4-triazol-1-yl)-3-(4-chlorophenyl)-propane, 1-(5-methyl-1,3-dioxan-5-yl)-1-acetoxy-2-(1,2,4-triazol-1-yl)-3-(4-chlorophenyl)-propane, 1-(2-ethyl-5-methyl-1,3-dioxan-5-yl)-1-methoxy-2-(1,2,4-triazol-1-yl)-3-(4-chlorophenyl)-propane, 1-(2-ethyl-5-methyl-1,3-dioxan-5-yl)-1-n-propoxy-2-(1,2,4-triazol-1-yl)-3-(4-chlorophenyl)-propane, 1-(2-ethyl-5-methyl-1,3-dioxan-5-yl)-1-acetoxy-2-(1,2,4-triazol-1-yl)-3-(4-chlorophenyl)-propane, 1-(2-ethyl-5-methyl-1,3-dioxan-5-yl)-1-propionyloxy-2-(1,2,4-triazol-1-yl)-3-(4-chlorophenyl)-propane, 1-(2-ethyl-5-methyl-1,3-dioxan-5-yl)-1-butyryloxy-2-(1,2,4-triazol-1-yl)-3-(4-chlorophenyl)-propane, 1-(5-methyl-1,3-dioxan-5-yl)-2-(1,2,4-triazol-1-yl)-3-(4-bromophenyl)-propan-1-one, 1-(5-methyl-1,3-dioxan-5-yl)-2-(1,2,4-triazol-1-yl)-3-(4-bromophenyl)-propan-1-ol, 1-(2-ethyl-5-methyl-1,3-dioxan-5-yl)-2-(1,2,4-triazol-1-yl)-3-(4-bromophenyl)-propan-1-one, 1-(2-ethyl-5-methyl-1,3-dioxan-5-yl)-2-(1,2,4-triazol-1-yl)-3-(4-bromophenyl)-propan-1-ol, 1-(5-methyl-1,3-dioxan-5-yl)-1-acetoxy-2-(1,2,4-triazol-1-yl)-3-(4-bromophenyl)-propane, 1-(2-ethyl-5-methyl-1,3-dioxan-5-yl)-1-acetoxy-2-(1,2,4-triazol-1-yl)-3-(4-bromophenyl)-propane, 1-(5-methyl-1,3-dioxan-5-yl)-2-(1,2,4-triazol-1-yl)-3-(2,4-dichlorophenyl)-propan-1-one, 1-(5-methyl-1,3-dioxan-5-yl)-2-(1,2,4-triazol-1-yl)-3-(2,4-dichlorophenyl)-propan-1-ol, 1-(2-ethyl-5-methyl-1,3- dioxan-5-yl)-2-(1,2,4-triazol-1-yl)-3-(2,4-dichlorophenyl)-propan-1-one, 1-(2-ethyl-5-methyl-1,3-dioxan-5-yl)-2-(1,2,4-triazol-1-yl)-3-(2,4-dichlorophenyl)-propan-1-ol, 1-(2,5-methyl-1,3-dioxan-5-yl)-2-(1,2,4-triazol-1-yl)-3-(2,4-dichlorophenyl)-propan-1-one, 1-(2,5-diethyl-1,3-dioxan-5-yl)-2-(1,2,4-triazol-1-yl)-3-(2,4-dichlorophenyl)-propan-1-ol, 1-(2-n-propyl-5-methyl-1,3-dioxan-5-yl)-2-(1,2,4-triazol-1-yl)-3-(2,4-dichlorophenyl)-propan-1-ol, 1-(2-n-propyl-5-methyl-1,3-dioxan-5-yl)-2-(1,2,4-triazol-1-yl)-3-(2,4-dichlorophenyl)-propan-1-one, 1-(2-isopropyl-5-methyl-1,3-dioxan-5-yl)-2-(1,2,4-triazol-1-yl)-3-(2,4-dichlorophenyl)-propan-1-one, 1-(2-isopropyl-5-methyl-1,3-dioxan-5-yl)-2-(1,2,4-triazol-1-yl)-3-(2,4-dichlorophenyl)-propan-1-ol, 1-(2-n-butyl-5-methyl-1,3-dioxan-5-yl)-2-(1,2,4-triazol-1-yl)-3-(2,4-dichlorophenyl)-propan-1-one, 1-(2-n-butyl-5-methyl-1,3-dioxan-5-yl)-2-(1,2,4-triazol-1-yl)-3-(2,4-dichlorophenyl)-propan-1-ol, 1-(2-tert.-butyl-5-methyl-1,3-dioxan-5-yl)-2-(1,2,4-triazol-1-yl)-3-(2,4-dichlorophenyl)-propan-1-one, 1-(2-tert.-butyl-5-methyl-1,3-dioxan-5-yl)-2-(1,2,4-triazol-1-yl)-3-(2,4-dichlorophehyl)-propan-1-ol, 1-(5-methyl-1,3-dioxan-5-yl)-1-acetoxy-2-(1,2,4-triazol-1-yl)-3-(2,4-dichlorophenyl)-propane, 1-(5-methyl-1,3-dioxan-5-yl)-1-propenyloxy-2-(1,2,4-triazol-1-yl)-3-(2,4-dichlorophenyl)-propane, 1-(2-ethyl-5-methyl-1,3-dioxan-5-yl)-1-acetoxy-2-(1,2,4-triazol-1-yl)-3-(2,4-dichlorophenyl)-propane, 1-(2-isopropyl-5-methyl-1,3-dioxan-5-yl)-1-acetoxy-2-(1,2,4-triazol-1-yl)-3-(2,4-dichlorophenyl)-propane, 1-(5-methyl-1,3-dioxan-5-yl)-2-(1,2,4-triazol-1-yl)-3-(3,4-dichlorophenyl)-propan-1-one, 1-(5-methyl-1,3-dioxan-5-yl)-2-(1,2,4-triazol-1-yl)-3-(3,4-dichlorophenyl)-propan-1-ol, 1-(2-ethyl-5-methyl-1,3-dioxan-5-yl)-2-(1,2,4-triazol-1-yl)-3-(3,4-dichlorophenyl)-propan-1-ol, 1-(2-ethyl-5-methyl-1,2-dioxan-5-yl)-2-(1,2,4-triazol-1-yl)-3-(3,4-dichlorophenyl)-propan-1-one, 1-(2-ethyl-5-methyl-1,2-dioxan-5-yl)-1-acetacetoxy-2-(1,2,4-triazol-1-yl)-3-(3,4-dichlorophenyl)-propane, 1-(2-ethyl-5-propyl-1,2-dioxan-5-yl)-1-benzoyl-2-(1,2,4-triazol-1-yl)-3-(3,4-dichlorophenyl)-propane, 1-(5-methyl-1,2-dioxan-5-yl)-2-(1,2,4-triazol-1-yl)-3-(4-methylphenyl)-propan-1-one, 1-(5-methyl-1,3-dioxan-5-yl)-2-(1,2,4-triazol-1-yl)-3-(4-methylphenyl)-propan-1-ol, 1-(2-ethyl-5-methyl-1,3-dioxan-5-yl)-2-(1,2,4-triazol-1-yl)-3-(4-methylphenyl)-propan-1-one, 1-(2-ethyl-5-methyl-1,3-dioxan-5-yl)-2-(1,2,4-triazol-1-yl)-3-(4-methylphenyl)-propan-1-ol, 1-(5-methyl-1,3-dioxan-5-yl)-2-(1,2,4-triazol-1-yl)-3-(3-methylphenyl)-propan-1-one, 1-(5-methyl-1,3-dioxan-5-yl)-2-(1,2,4-triazol-1-yl)-3-(3-methylphenyl)-propan-1-ol, 1-(5-methyl-1,3-dioxan-5-yl)-2-(1,2,4-triazol-1-yl)-3-(4-ethylphenyl)-propan-1-one, 1-(5-methyl-1,3-dioxan-5-yl)-2-(1,2,4-triazol-1-yl)-3-(4-ethylphenyl)-propan-1-ol, 1-(5-methyl-1,3-dioxan-5-yl)-2-(1,2,4-triazol-1-yl)-3-(3,4-dimethylphenyl)-propan-1-one, 1-(5-methyl-1,3-dioxan-5-yl)-2-(1,2,4-triazol-1-yl)-3-(3,4-dimethylphenyl)-propan-1-ol, 1-(2-ethyl-5-methyl-1,3-dioxan-5-yl)-2-(1,2,4-triazol-1-yl)-3-(4-methoxyphenyl)-propan-1-one, 1-(2-ethyl-5-methyl-1,3-dioxan-5-yl)-2-(1,2,4-triazol-1-yl)-3-(4-methoxyphenyl)-propan-1-ol, 1-(2-ethyl-5-methyl-1,3-dioxan-5-yl)-2-(1,2,4-triazol-1-yl)-3-(4-nitrophenyl)-propan-1-one, 1-(5-methyl-1,3-dioxan-5-yl)-2-(1,2,4-triazol-1-yl)-3-(4-trifluoromethylphenyl)-propan-1-one, 1-(5-methyl-1,3-dioxan-5-yl)-2-(1,2,4-triazol-1-yl)-3β-(4-trifluoromethylphenyl)-propan-1-ol, 1-(2-ethyl-5-methyl-1,3-dioxan-5-yl)-2-(1,2,4-triazol-1-yl)-3-(4-trifluoromethylphenyl)-propan-1-one, 1-(2-ethyl-5-methyl-1,3-dioxan-5-yl)-2-(1,2,4-triazol-1-yl)-3-(4-trifluoromethylphenyl)-propan-1-ol, 1-(2-ethyl-5-methyl-1,3-dioxan-5-yl)-2-(1,2,4-triazol-1-yl)-3-(4-tert.-butylphenyl)-propan-1-one, 1-(5-methyl-1,3-dioxan-5-yl)-2-(1,2,4-triazol-1-yl)-3-(4-ethoxyphenyl)-propan-1-one and 1-(5-methyl-1,3-dioxan-5-yl)-2-(1,2,4-triazol-1-yl)-3-(4-ethoxyphenyl)-propan-1-one.

The Examples which follow illustrate the preparation of the compounds.

EXAMPLE 1

(a) Preparation of the starting material

A solution of 498 g (1 mole) of pyrrolidone-bromine complex in 1 liter of tetrahydrofuran is added dropwise, in the course of 2 hours, at 50° C., to a solution of 144 g (1 mole) of 5-acetyl-5-methyl-1,3dioxane and 85.5 g (1 mole) of pyrrolidone in 500 ml of tetrahydrofuran. The mixture is then stirred for eight hours at 50° C., the white precipitate of pyrrolidone hydrobromide is filtered off and washed with 50 ml of tetrahydrofuran, and the filtrate is concentrated under reduced pressure. 220 g (99%) of crude oily 1-(5-methyl-1,3-dioxan-5-yl)-2-bromoethan-1-one are obtained.

A solution of 223 g (1 mole) of 1-(5-methyl-1,3-dioxan-5-yl)-2-bromoethan-1-one in 200 ml of tetrahydrofuran is added dropwise in the course of 2 hours, at 25° C., to a suspension, which is stirred under pure nitrogen, of 100.1 g (1.1 moles) of sodium 1,2,4-triazolide in 300 ml of dry tetrahydrofuran. After refluxing the mixture for eight hours, the inorganic precipitate is filtered off and the filtrate is concentrated to half its volume. The mixture is seeded and left to stand overnight at +3° C. The precipitate is filtered off, washed with 30 ml of cold tetrahydrofuran (at +5° C.), then with 80 ml of ether and thereafter with 100 ml of n-pentane, and dried. 184 g (87.2%) of 1-(5-methyl-1,3-dioxan-5-yl)-2-(1,2,4-triazol-1-yl)-ethan-1-one are obtained as white crystals of melting point 95°–97° C.

(b) Preparation of the end product

A solution of 105.5 g (0.5 mole) of 1-(5-methyl-1,3-dioxan-5-yl)-2-(1,2,4-triazol-1-yl)-ethan-1-one in 100 ml of dimethylformamide is added dropwise, at 20°–25° C., to a suspension, stirred under pure nitrogen, of 13.2 g (0.55 mole) of sodium hydride in 100 ml of dry dimethylformamide. The reaction mixture is then stirred for three hours at 25° C., after which a solution of 81 g (0.5 mole) of 4-chlorobenzyl chloride in 50 ml of dimethylformamide is added dropwise and stirring is then continued for 14 hours. 50 ml of ice water are then cautiously added dropwise and the mixture is concentrated under reduced pressure. The residue is partitioned between 400 ml of methylene chloride and 200 ml of water and the organic phase is washed with three times 200 ml of water, dried over $Na_2SO_4$ and evaporated down. 112 g (66.8%) of 1-(5-methyl-1,3-dioxan-5-yl)-2-(1,2,4-triazol-1-yl)-3-(4-chlorophenyl)-propan-1-one are obtained as a pale yellow resin.

$^1$H-NMR (80 MHz/CDCl$_3$): δ=0.87 (s, 3H), 3.1–3.6 (m, 4H), 3.95–4.4 (t, 2H), 4.5–5.0 (2 dd, 2H in total), 5.65–5.95 (q, 1H), 6.8–7.3 (m, 4H), 7.8 (s, 1H) and 8.0 ppm (s, 1H).

EXAMPLE 2

11.5 g (0.3 mole) of sodium borohydride are added, a little at a time, to a solution of 90 g (0.269 mole) of 1-(5-methyl-1,3-dioxan-5-yl)-2-(1,2,4-triazol-1-yl)-3-(4-chlorophenyl)-propan-1-one in 250 ml of methanol, at from 0° to +5° C. The mixture is stirred for 12 hours at 20° C. and is then evaporated down. The residue is stirred for 1 hour with 200 ml of 20% strength potassium hydroxide solution and the mixture is then extracted with 500 ml of methylene chloride. The organic phase is washed with three times 50 ml of water, dried over sodium sulfate and evaporated down. The residue crystallizes at +5° C. after addition of 20 ml of ether. 45 g (49.6%) of 1-(5-methyl-1,3-dioxan-5-yl)-2-(1,2,4-triazol-1-yl)-3-(4-chlorophenyl)-propan-1-ol are isolated as white crystals of melting point 152°–154° C.

EXAMPLE 3

A mixture of 15.2 g (0.045 mole) of 1-(5-methyl-1,3-dioxan-5-yl)-2-(1,2,4-triazol-1-yl)-3-(4-chlorophenyl)-propan-1-ol, 100 g of 1-chloropropane, 3 g of tetrabutylammonium bisulfate and 65 g of 50% strength sodium hydroxide solution is heated for 36 hours at 30° C., with vigorous stirring. 300 ml of water are then added and the batch is extracted with twice 150 ml of methylene chloride. The combined extracts are extracted by shaking with eight time 100 ml of water, dried over magnesium sulfate and evaporated down. The residue crystallizes after addition of 20 ml of petroleum ether and 5 ml of ether. 12 g (70.3%) of 1-(5-methyl-1,3-dioxan-5-yl)-1-n-propoxy-2-(1,2,4-triazol-1-yl)-3-(4-chlorophenyl)-propane are obtained as white crystals of melting point 94°–96° C.

EXAMPLE 4

A solution of 23.6 g (0.07 mole) of 1-(5-methyl-1,3-dioxan-5-yl)-2-(1,2,4-triazol-1-yl)-3-(4-chlorophenyl)-propan-1-ol in 100 ml of tetrahydrofuran is added dropwise to a suspension of 2.4 g of sodium hydride in 120 ml of dry tetrahydrofuran. After stirring the mixture for 12 hours at 25° C, a solution of 9.7 g (0.08 mole) of allyl bromide in 20 ml of tetrahydrofuran is added dropwise. The reaction mixture is stirred for 36 hours, 20 ml of water are then added cautiously, and the batch is evaporated down. The residue is taken up in 350 ml of methylene chloride, the solution is washed with three times 100 ml of water, and the organic phase is dried and evaporated down. The residue is mixed with 30 ml of petroleum ether and 10 ml of ether and left to stand overnight at +3° C. The crystalline, colorless precipitate is filtered off, washed with petroleum ether and dried. 22.6 g (87.5%) of 1-(5-methyl-1,3-dioxan-5-yl)-1-allyloxy-2-(1,2,4-triazol-1-yl)-3-(4-chlorophenyl)-propane, of melting point 113°–115° C., are obtained.

EXAMPLE 5

A mixture of 20 g (0.053 mole) of 1-(5-methyl-1,3-dioxan-5-yl)-2-(1,2,4-triazol-1-yl)-3-(2,4-dichlorophenyl)-propan-1-ol. (cf. Example 35), 2 g of imidazole and 100 ml of propionic anhydride is stirred for 10 hours at 60° C. and then evaporated down under reduced pressure. The residue is dissolved in 250 ml of ether and the solution is stirred for 30 minutes with 100 ml of a 6% strength sodium bicarbonate solution. The organic phase is dried over sodium sulfate and evaporated down under reduced pressure, ultimately at 50° C. and 0.1 mbar. 17.1 g (75.4%) of 1-(5-methyl-1,3-dioxan-5-yl)-1-acetoxy-(1,2,4-triazol-1-yl)-3-(2,4-dichlorophenyl)-propane are obtained as a pale brown resin.

$^1$H-NMR (80 MHz/CDCl$_3$): δ=0.85 (s, 3H), 1.15–1.4 (t, 3H), 2.4–3.2 (q, 2H), 3.3–3.6 (m, 2H), 3.8–4.2 (m, 2H), 4.6–5.1 (2 dd, 2H in total), 6.1 (s, 1H), 6.5–7.6 (2 tt, 4H in total), 8.1 (s, 1H) and 8.28 ppm (s, 1H).

The compounds listed in the Table which follows can be prepared in a similar manner.

| Ex. no. | Ar | R$^1$ | R$^2$ | X | m.p./°C. IR (film) [cm$^{-1}$] |
|---|---|---|---|---|---|
| 6 | C$_6$H$_5$— | CH$_3$ | H | —CO— | 96–98 |
| 7 | C$_6$H$_5$— | CH$_3$— | H | OH<br>\|<br>—CH— | 172–174 |
| 8 | 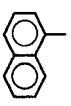 | CH$_3$— | H | —CO— | 97–99 |
| 9 | 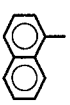 | CH$_3$— | H | OH<br>\|<br>—CH— | 174–176 |
| 10 | 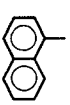 | CH$_3$— | H | O—COCH$_3$<br>\|<br>—CH— | 148–150 |
| 11 | 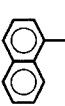 | CH$_3$— | C$_2$H$_5$— | —CO— | 128–129 |
| 12 | 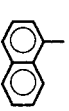 | CH$_3$— | C$_2$H$_5$ | OH<br>\|<br>—CH— | resin 3105, 3055, 2950, 2845 1592, 1365, 1212, 1156, 775 |

-continued

| Ex. no. | Ar | R¹ | R² | X | m.p./°C. IR (film) [cm⁻¹] |
|---|---|---|---|---|---|
| 13 | F—⟨C₆H₄⟩— | CH₃— | H | —CO— | 88–90 |
| 14 | F—⟨C₆H₄⟩— | CH₃— | H | OH<br>\|<br>—CH— | 140–142 |
| 15 | Cl—⟨C₆H₄⟩— | CH₃— | H | O<br>\|<br>—CH— | 66–68 |
| 16 | Cl—⟨C₆H₄⟩— | CH₃— | C₂H₅— | —CO— | resin 3095, 2950, 2835, 1695, 1472, 1260, 1147, 1125, 1080, 805, 670 |
| 17 | Cl—⟨C₆H₄⟩— | CH₃— | C₂H₅— | OH<br>\|<br>—CH— | 144–145 |
| 18 | Cl—⟨C₆H₄⟩— | CH₃— | C₂H₅— | O<br>\|<br>—CH— | 83–84 |
| 19 | Cl—⟨C₆H₄⟩— | CH₃— | n-C₃H₇— | —CO— | resin 3110, 2960, 2870, 1712, 1490, 1274, 1100, 1022, 812, 705, 678 |
| 20 | Cl—⟨C₆H₄⟩— | CH₃— | n-C₃H₇— | OH<br>\|<br>—CH— | 125–130<br>diastereoisomer I |
| 21 | Cl—⟨C₆H₄⟩— | CH₃— | n-C₃H₇— | OH<br>\|<br>—CH—<br>diastereoisomeric mixture | resin 3200, 2960, 2860, 1505, 1490, 1268, 1158, 1130, 1095, 1020, 930, 825, 810 |
| 22 | Cl—⟨C₆H₄⟩— | CH₃— | —CH(CH₃)₂ | OH<br>\|<br>—CH—<br>diastereoisomer I | 135–155 |
| 23 | Cl—⟨C₆H₄⟩— | CH₃— | —CH(CH₃)₂ | OH<br>\|<br>—CH—<br>diastereoisomeric mixture | resin 3270, 2960, 2870, 1886, 1390, 12.., 1130, 1090, 804, 950, 672 |
| 24 | Cl—⟨C₆H₄⟩— | CH₃— | n-C₄H₉ | OH<br>\|<br>—CH—<br>diastereoisomer I | 123–133 |
| 25 | Cl—⟨C₆H₄⟩— | CH₃— | n-C₄H₉ | OH<br>\|<br>—CH—<br>diastereoisomeric mixture | resin 2260, 3095, 2955, 2850, 1505, 140.., 1274, 1102, 1082, 812 |
| 26 | Br—⟨C₆H₄⟩— | CH₃— | H | —CO— | resin 3105, 2965, 2842, 1705, 1470, 13.., 1253, 1150, 1080, 775, 670 |
| 27 | Br—⟨C₆H₄⟩— | CH₃— | H | OH<br>\|<br>—CH— | 156–158 |
| 28 | Br—⟨C₆H₄⟩— | CH₃— | C₂H₅ | —CO— | resin 3102, 2960, 2920, 2845, 1705, 1475, 1390, 1260, 1150, 1080, 800, 668 |
| 29 | Br—⟨C₆H₄⟩— | CH₃— | C₂H₅— | OH<br>\|<br>—CH—<br>diastereoisomer I | 172–173 |

-continued

| Ex. no. | Ar | R¹ | R² | X | m.p./°C. IR (film) [cm⁻¹] |
|---|---|---|---|---|---|
| 30 | Br–⟨C₆H₄⟩– | $CH_3$– | $C_2H_5$– | OH<br>\|<br>–CH–<br>diastereoisomeric mixture | resin 3260, 3020, 2960, 2850, 1495, 1385, 1260, 1125 |
| 31 | 3,4-Cl₂–⟨C₆H₃⟩– | $CH_3$– | $C_2H_5$ | –CO– | resin 3106, 2965, 2850, 1705, 1460, 1385, 1265, 1125, 1024, 918, 810, 750, |
| 32 | 3,4-Cl₂–⟨C₆H₃⟩– | $CH_3$– | $C_2H_5$– | OH<br>\|<br>–CH–<br>diastereoisomer I | 171–173 |
| 33 | 3,4-Cl₂–⟨C₆H₃⟩– | $CH_3$– | $C_2H_5$– | OH<br>\|<br>–CH–<br>diastereoisomeric mixture | resin 3200, 2985, 2840, 1460, 1384, 126., 1120, 1020, 910, 815, 692 |
| 34 | 3,4-Cl₂–⟨C₆H₃⟩– | $CH_3$– | H | –CO– | 118–120 |
| 35 | 2,4-Cl₂–⟨C₆H₃⟩– | $CH_3$– | H | OH<br>\|<br>–CH– | 133–136 |
| 36 | 2,4-Cl₂–⟨C₆H₃⟩– | $CH_3$– | $C_2H_5$– | –CO– | resin 3100, 2955, 2840, 1698, 1570, 1458, 1260, 1150, 1125, 1090, 920, 825 |
| 37 | 2,4-Cl₂–⟨C₆H₃⟩– | $CH_3$– | $C_2H_5$– | OH<br>\|<br>–CH– | 138–143 |
| 38 | 3,4-Cl₂–⟨C₆H₃⟩– | $CH_3$– | n-$C_3H_7$– | –CO– | resin 3100, 2950, 2860, 1705, 1580, 1466, 1380, 1268, 1096, 825, 672 |
| 39 | 3,4-Cl₂–⟨C₆H₃⟩– | $CH_3$– | n-$C_3H_7$ | OH<br>\|<br>–CH– | 127–129 |
| 40 | 3,4-Cl₂–⟨C₆H₃⟩– | $CH_3$– | –CH(CH₃)₂ | –CO– | resin 3105, 2950, 2860, 1705, 1578, 1460, 1380, 1260, 1155, 1095, 922, 825, 670 |
| 41 | 3,4-Cl₂–⟨C₆H₃⟩– | $CH_3$– | –CH(CH₃)₂ | OH<br>\|<br>–CH–<br>diastereoisomer I | 141–143 |
| 42 | 3,4-Cl₂–⟨C₆H₃⟩– | $CH_3$– | –CH(CH₃)₂ | OH<br>\|<br>–CH–<br>diastereoisomeric mixture | resin 3130, 2955, 2855, 1735, 1466, 1360, 1228, 1130, 1098, 940, 910, 860 |
| 43 | 3,4-Cl₂–⟨C₆H₃⟩– | $CH_3$– | –CH(CH₃)₂ | O–COCH₃<br>\|<br>–CH– | 118–128 |

-continued

| Ex. no. | Ar | R¹ | R² | X | m.p./°C. IR (film) [cm⁻¹] |
|---|---|---|---|---|---|
| 44 | 2,4-Cl₂-C₆H₃- | CH₃- | n-C₄H₉ | —CO— | resin 3100, 2950, 2855, 1706, 1580, 1465, 1264, 1150, 1095, 920, 824, 668 |
| 45 | 2,4-Cl₂-C₆H₃- | CH₃ | n-C₄H₉ | —CH(OH)— | 153–165 |
| 46 | 2,4-Cl₂-C₆H₃- | CH₃- | n-C₄H₉ | —CH(O—COCH₃)— | Harz 3110, 2950, 2850, 1740, 1467, 1220, 1130, 1100, 1025, 948, 905, 812, 67. |
| 47 | 2,4-Cl₂-C₆H₃- | CH₃- | —C(CH₃)₃ | —CO— | 165–168 |
| 48 | 2,4-Cl₂-C₆H₃- | CH₃- | —C(CH₃)₃ | —CH(OH)— | resin 3320, 2960, 2860, 1465, 1267, 1188, 1128, 1095, 860, 820, 692 |
| 49 | 3-CH₃-C₆H₄- | CH₃ | H | —CO— | 53–55 |
| 50 | 3-CH₃-C₆H₄- | CH₃- | H | —CH(OH)— | 128–130 |
| 51 | 4-CH₃-C₆H₄- | CH₃- | H | —CO— | 112–114 |
| 52 | 4-CH₃-C₆H₄- | CH₃- | H | —CH(OH)— | 114–116 |
| 53 | 4-CH₃-C₆H₄- | CH₃- | C₂H₅ | —CO— | resin 3110, 2965, 2850, 1706, 1490, 1380, 1265, 1155, 1082, 915, 800, 630 |
| 54 | 4-CH₃-C₆H₄- | CH₃- | C₂H₅- | —CH(OH)— diastereoisomer I | 161–162 |
| 55 | 4-CH₃-C₆H₄- | CH₃- | C₂H₅- | —CH(OH)— diastereoisomeric mixture | resin 3280, 2965, 2845, 1500, 1385, 1262, 1190, 1080, 918, 870, 800, 670 |
| 56 | 4-C₂H₅-C₆H₄- | CH₃- | H | —CO— | 59–60 |
| 57 | 4-C₂H₅-C₆H₄- | CH₃- | H | —CH(OH)— | 111–114 |
| 58 | 3,4-(CH₃)₂-C₆H₃- | CH₃- | H | —CO— | resin 3118, 2970, 2855, 1710, 1492, 1267, 1155, 1078, 920, 807, 672 |

-continued

| Ex. no. | Ar | R¹ | R² | X | m.p./°C. IR (film) [cm⁻¹] |
|---|---|---|---|---|---|
| 59 | 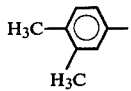 | CH₃— | H | OH<br>\|<br>—CH— | 127–128 |
| 60 |  | CH₂— | —CH(CH₃)₂ | —CO— | resin 3100, 2960, 2840, 1710, 1270, 1120, 1080, 1025, 810, 705, 678 |
| 61 | 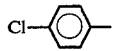 | CH₃— | n-C₄H₉— | —CO— | resin 3105, 2950, 2845, 1705, 1260, 1150, 1125, 1080, 1022, 808, 670 |
| 62 | 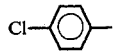 | C₂H₅— | C₂H₅— | —CO— | 89–91 |
| 63 | 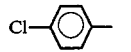 | C₂H₅— | C₂H₅— | OH<br>\|<br>—CH— | 115–117 |
| 64 | 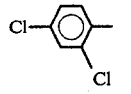 | C₂H₅ | C₂H₅— | —CO— | 61–63 |
| 65 |  | C₂H₅— | C₂H₅ | OH<br>\|<br>—CH— | 113–115 |

The new compounds may influence practically all the development stages of a plant in different ways; they are therefore used as growth regulators.

The diversity of action of growth regulators depends especially on (a) the type and variety of plant;

(b) the time applied, with reference to the development stage of the plants and the time of year;

(c) the place and method of application (seed treatment, soil treatment, or application to leaves);

(d) climatic factors (sunshine duration, average temperature, precipitate);

(e) soil conditions (including fertilization);

(f) the formulation or application form of the active ingredient; and (g) the concentration at which the active ingredient is applied.

A description of some of the various possibilities of using growth regulators in agriculture and horticulture is given below.

A. With the compounds according to the invention, vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embarkments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton.

It is thus possible for this important crop to be harvested completely mechanically.

Growth regulators may also increase or inhibit lateral branching. This is of interest when it is desired to inhibit, for instance in tobacco plants, the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-suspectible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased suspectibility to freeze injury and—because of the relatively low leaf or plant mass—attack by various diseases, especially fungus diseases. The inhibition of vegetative growth also makes closer planting possible in numerous crops, which means an increase in yield, based on the area cropped.

B. Better yields both of plant parts and plant materials may be obtained with the active ingredients according to the invention. It is thus for instance possible to induce increased formation of buds, blossom, leaves, fruit, seed grains, roots and tubers, to increase the sugar content of sugar beets, sugarcane and citrus fruit, to raise the protein content of cereals and soybeans, and to stimulate the increased formation of latex in rubber trees.

The compounds according to the invention may raise the yield by influencing plant metabolism or by promoting or inhibiting vegetative and/or generative growth.

C. Finally, it is also possible with growth regulators to shorten or lengthen growth stages and to accelerate or retard the ripening process in plant parts either before or after harvesting.

A factor of economical interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of plants.

The action of the compounds according to the invention is superior to that of prior art growth regulators. This action is manifested not only in monocotyledon crops, e.g., cereals such as wheat, barley, rye, oats, rice, Indian corn or grasses, but also particularly in dicotyledons (e.g., sunflowers, tomatoes, groundnuts, grapes, cotton, rape, and, particularly, soybeans) and various ornamentals such as chrysanthemums, poinsettias and hibiscus.

The compounds according to the invention may be applied to the crop either by treating the seed, treating the soil, i.e., through the roots, or—a particularly preferred embodiment—by spraying the leaves. Because the active ingredients are well tolerated by the crop plants, application rates may vary within a wide range.

When the active ingredients are used to treat seed, active ingredient amounts of from 0.001 to 50 g, preferably from 0.01 to 10 g, per kg of seed are generally required.

When the active ingredients are applied to the soil or foliage, amounts of from 0.1 to 12 kg/ha, preferably from 0.25 to 3 kg/ha, are generally considered to be sufficient.

The compounds of the invention can be applied in conventional formulations, e.g. solutions, emulsions, suspensions, dusts, powders, pastes and granules. The form of application depends entirely on the purpose for which the agents are being used; in should, however, ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g., xylene and benzene, chloroaromatics, e.g. chlorobenzene, paraffin, e.g. petroleum fractions, alcohols, e.g. methanol and butanol, amines, e.g. ethanolamine, and dimethylformamide and water; carriers, for example natural rock powders, e.g. kaolin, alumina, talc and chalk, and synthetic rock powders, e.g. highly disperse silica and silicates; emulsifiers and other surfactants, for example non-ionic and anionic emulsifiers, e.g. polyoxyethylene fatty alcohol ethers, alkylsulfonates and arylsulfonates, and dispersants, for example lignin, sulfite waste liquors and methylcellulose. The compounds according to the invention are preferably applied in aqueous solution, if desired together with water-miscible organic solvents, such as methanol or other lower alcohols, acetone, dimethylformamide or N-methylpyrrolidone. The formulations generally contain from 0.1 to 95, and preferably from 0.5 to 90, wt% of active ingredient.

The formulations, and the ready-to-use preparations obtained therefrom, e.g. solutions, emulsions, suspensions, powders, dusts, pastes or granules, are applied in the conventional manner, e.g. preemergence, postemergence, or as seed disinfectants.

Examples of formulations are as follows:

I. 20 parts by weight of the compound of Example 7 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

II. 3 parts by weight of the compound of Example 29 is intimately mixed with 97 parts by weight of particulate kaolin. A dust is obtained containing 3% by weight of the active ingredient.

III. 30 parts by weight of the compound of Example 35 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV. 40 parts by weight of the compound of Example 37 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

V. 20 parts of the compound of Example 52 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

VI. 90 parts by weight of the compound of Example 1 is mixed with 10 parts by weight of N-methyl-α-pyrrolidone. A mixture is obtained which is suitable for application in the form of very fine drops.

VII. 20 parts by weight of the compound of Example 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

VIII. 20 parts by weight of the compound of Example 12 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IX. 20 parts by weight of the compound of Example 17 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the sultion into 100,000 parts by weight of water and uniformly distributing it therein, an aqueous dispersion is obtained containing 0.02% by weight of the active ingredient.

The agents according to the invention may, in these application forms, also be mixed and applied with other active ingredients, e.g., herbicides, insecticides, other growth regulators, fungicides and fertilizers. When mixed with other growth regulators, the spectrum of action is in many cases increased; with a number of these compositions, synergistic effects also occur; i.e., the action of the combination product is greater than the effect of the individual components added together.

Examples of fungicides which may be combined with the compounds according to the invention are dithiocarbamates and derivatives thereof, such as
Ferric dimethyldithiocarbamate
zinc dimethyldithiocarbamate
manganese ethylenebisdithiocarbamate
zinc ethylenebisthiocarbamate
tetramethylthiuram disulfide
manganese-zinc ethylenediamine-bisdithiocarbamate
zinc-(,N,N'-propylene-bisdithiocarbamate)
ammonia complex of zinc-(N,N'-ethylene)-bisdithiocarbamate and
N,N'-polyethylene-bis-(thiocarbamoyl)-disulfide ammonia complex of zinc-(N,N'-propylene-bisdithiocarbamate) and
N,N'-polypropylene-bis-(thiocarbamoyl)-disulfide nitrophenol derivatives, such as dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
heterocyclic structures, such as
N-trichloromethylthiotetrahydrophthalimide
N-trichloromethylthiophthalimide
2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl]-3-phenyl-1,2,4-triazole
5-ethoxy-3-trichloromethyl-1,2,4-thiadiazole
2,3-dicyano-1,4-dithiaanthraquinone
2-thio-1,3-dihtio-(4,5-b)-quinoxaline
methyl 1-(butylcarbamoyl)-2-benzimidazole carbamate
2-methoxycarbonylaminobenzimidazole
2-thiocyanomethylthiobenzothiazole
4-(2-chlorophenylhydrazono)-3-methyl-5-isooxazolone
pyridine-2-thiol-1-oxide
8-hydroxyquinoline and its copper salt
2,3-dihydro-5-carboxanilido-6-methyl-1,4-oxathiin-4,4-dioxide
2,3-dihydro-5-carboxanilido-6-methyl-1,4-oxathiin
2-[furyl-(2)]-benzimidazole piperazine-1,4-diyl-bis[1-(2,2,2-trichloroethyl)-formamide]
2-[thiazolyl-(4)]-benzimidazole
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene and various fungicides, such as dodecylguanidine acetate
3-[2-(3,5-dimethyl-2-oxycyclohexyl)-2-hydroxyethyl]-glutarimide hexachlorobenzene
N-dichlorofluoromethylthio-N,N'-dimethyl-N-phenylsulfuric acid diamide
N-dichlorofluoromethylthio-N-methyl-N'-methyl-N-phenylsulfuric acid diamide
D,L-methyl-N-(2,6-dimethylphenyl)-N-fur-2-yl-alanate methyl D,L-N-(2,6-dimethylphenyl)-N-(2'-methoxyacetyl)-alanate diisopropyl 5-nitroisophthalate
2,5-dimethylfuran-3-carboxylic acid anilide
2,5-dimethylfuran-3-carboxylic acid cyclohexylamide
2-methylbenzoic acid anilide
1-(3,4-dichloroanilino)-1-formylamino-2,2,2-trichloroethane
2,6-dimethyl-N-tridecylmorpholine and its salts
2,6-dimethyl-N-cyclododecylmorpholine and its salts
2,3-dichloro-1,4-naphthoquinone
1,4-dichloro-2,5-dimethoxybenzene
p-dimethylaminobenzene diazosodium sulfonate
1-chloro-2-nitropropane
polychloronitrobenzenes such as pentachloronitrobenzene methyl isocyanate
fungicidal antibiotics, e.g., griseofulvin and kasugamycin tetrafluorodichloroacetone
1-phenylthiosemicarbazide
Bordeaux mixture
nickel-containing compounds, and sulfur.

The following examples demonstrate the action of the compounds according to the invention as growth regulators; however, further applications as growth regulators are not excluded.

Greenhouse experiment

Plastic pots approx. 12.5 cm in diameter were filled with a peat culture substrate provided with sufficient nutrients, and test plants grown therein. In the preemergence treatment, the substances to be tested were sprayed, as aqueous formulations at various concentrations, onto the surface of the soil on the day the seeds were sown. In the postemergence treatment, the plants were sprayed with aqueous formulations. The growth-regulating action observed was confirmed at the end of the experiment by height measurement. The values obtained were compared with those for untreated plants.

In these experiments, which were carried out on lawns and in tomatoes and soybeans, particularly the compounds of Examples 1,2, 7, 13, 16 to 26, 34, 37, 38, 41 to 43, 45 and 52 exhibited a better action than chlorocholine hydrochloride and 3,3-dimethyl-2-(1,2,4-thiazol-1 yl)-chlorobenzoyl)-butane.

We claim:

1. A compound of the formula I

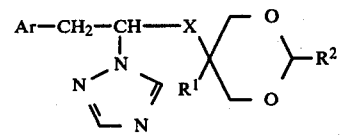

where $R^1$ and $R^2$ are identical or different and each is hydrogen or alkyl of 1 to 5 carbon atoms, Ar is furanyl, thienyl, biphenylyl or naphthyl, or is phenyl which is unsubstituted or substituted by fluorine, chlorine, bromine, iodine, nitro or trifluoromethyl, or by alkyl, alkoxy or alkenyl, each of 1 to 5 carbon atoms, or by phenoxy, and X is —CO—, —CH(OH)— or —CH(OR$^3$)—, where $R^3$ is unsubstituted or chlorine substituted alkyl of 1 to 8 carbon atoms, or unsubstituted or chlorine-substituted alkenyl of 2 to 5 carbon atoms, or alkynyl of 3 or 4 carbon atoms or benzyl which is unsubstituted or substituted by fluorine, chlorine, bromine, nitro or trifluoromethyl or by alkyl or alkoxy of 1 to 4 carbon atoms, or $R^3$ is —CO—$R^4$, where $R^4$ is alkyl of 1 to 5 carbon atoms which is unsubstituted or substituted by halogen, alkenyl of 2 to 3 carbon atoms, alkoxy, oxo (=O) or carboxyalkyl.

2. A compound as claimed in claim 1 selected from the group consisting of 1-(5-methyl-1,3-dioxan-5-yl)-2-(1,2,4-triazol-1-yl)-3-phenyl-propan-1-one, 1-(5-methyl-1,3-dioxan-5-yl)-2-(1,2,4-triazol-1-yl)-3-phenyl-propan-1-ol, 1-(5-methyl-1,3-dioxan-5-yl)-2-(1,2,4-triazol-1-yl)-3-(naphth-1-yl)-propan-1-one, 1-(5-methyl-1,3-dioxan-5-yl)-2-(1,2,4-triazol-1-yl)-3-(naphth-1-yl)-propan-1-ol, 1-(5-methyl-1,3-dioxan-5-yl)-1-acetoxy-2-(1,2,4-triazol-1-yl)-3-(naphth-1-yl)-propane, 1-(2-ethyl-5-methyl-1,3-dioxan-5-yl)-2-(1,2,4-triazol-1-yl)-3-(naphth-1-yl)-propan-1-one, 1-(2-ethyl-5-methyl-1,3-dioxan-5-yl)-2-(1,2,4-triazol-1-yl)-3-(naphth-1-yl)-propan-1-ol, 1-(5-methyl-1,3-dioxan-5-yl)-2-(1,2,4-triazol-1-yl)-3-(4-fluorophenyl)-propan-1-one, 1-(5-methyl-1,3-dioxan-5-yl)-2-(1,2,4-triazol-1-yl)-3-(4-fluorophenyl)-propan-1-ol, 1-(5-methyl-1,3-dioxan-5-yl)-2-(1,2,4-triazol-1-yl)-3-(4-chlorophenyl)-propan-1-one, 1-(5-methyl-1,3-dioxan-5-yl)-2-(1,2,4-triazol-1-yl)-3-(4-chlorophenyl)-propan-1-ol, 1-(2-ethyl-5-methyl-1,3-dioxan-5-yl)-2-(1,2,4-triazol-1-yl)-3-(4-chlorophenyl)-propan-1-one, 1(2-ethyl-5-methyl-1,3-dioxan-5-yl)-2-(1,2,4-triazol-1-yl)-3-(4-chlorophenyl)-propan-1-ol, 1-(2-n-propyl-5-methyl-1,3-dioxan-5-yl)-2-(1,2,4-triazol-1-yl)-3-(4-chlorophenyl)-propan-1-one, 1-(2-n-propyl-5-methyl-1,3-dioxan-5-yl)-2-(1,2,4-triazol-1-yl)-3-(4-chlorophenyl)-propan-1-ol, 1-(5-methyl-1,3-dioxan-5-yl)-1-n-propoxy-2-(1,2,4-triazol-1-yl)-3-(4-chlorophenyl)-propane, 1-(5-methyl-1,3-dioxan-5-yl)-1-n-butoxy-2-(2-1,2,4-triazol-1-yl)-3-(4-chlorohenyl)-propane, 1-(5-methyl-1,3-dioxan-5-yl)-2-(1,2,4-triazol-1-yl)-3-(4-chlorophenyl)-propane, -1-one, 1-(2-ethyl-5-methyl-1,3-dioxan-5-yl)-1-n-propoxy-2-(1,2,4-triazol-1-yl)-3-(4-chlorophenyl)-propane, 1-(5-methyl-1,3-dioxan-5-yl)-2-(1,2,4-triazol-1-yl)-3-(4-bromophenyl)-propan-1-one, 1-(5-methyl-1,3-dioxan-5-yl)-2-(1,2,4-triazol-1-yl)-3-(4-bromophenyl)-propan-1-ol, 1-(2-ethyl-5-methyl-1,3-dioxan-5-yl)-2-(1,2,4-triazol-1-yl)-3-(4-bromophenyl)-propan-1-one, 1-(2-ethyl-5-methyl-1,3-dioxan-5-yl)-2-(1,2,4-triazol-1-yl)-3-(4-bromophenyl)-propan-1-ol, 1-(5-methyl-1,3-dioxan-5-yl)-2-(1,2,4-triazol-1-yl)-3-(2,4-dichlorophenyl)-propan-1-one, 1-(5-methyl-1,3-dioxan-5-yl)-2-(1,2,4-triazol-1-yl)-3-(2,4-dichlorophenyl)-propan-1-ol, 1-(2-ethyl-5-methyl-1,3-dioxan-5-yl)-2-(1,2,4-triazol-1-yl)-3-(2,4-dichlorophenyl)-propan-1-one, 1-(2-ethyl-5-methyl-1,3-dioxan-5-yl)-2-(1,2,4-triazol-1-yl)-3-(2,4-dichlorophenyl)-propan-1-ol, 1-(5-methyl-1,3-dioxan-5-yl)-2-(1,2,4-triazol-1-yl)-3-(3,4-dichlorophenyl)-propan-1-one, 1-(5-methyl-1,3-dioxan-5-yl)-2-(1,2,4-triazol-1-yl)-3-(3,4-dichlorophenyl)-propan-1-ol, 1-(5-methyl-1,3-dioxan-5-yl)-2-(1,2,4-triazol-1-yl)-3-(4-methylphenyl)-propan-1-one, 1-(5-methyl-1,3-dioxan-5-yl)-2-(1,2,4-triazol-1-yl)-3-(4-methylphenyl)-propan-1-ol, 1-(2-ethyl-5-methyl-1,3-dioxan-5-yl)-2-(1,2,4-triazol-1-yl)-3-(4-methylphenyl)-propan-1-one, 1-(2-ethyl-5-methyl-1,3-dioxan-5-yl)-2-(1,2,4-triazol-1-yl)-3-(4-methylphenyl)-propan-1-ol, 1-(5-methyl-1,3-dioxan-5-yl)-2-(1,2,4-triazol-1-yl)-3-(4-ethylphenyl)-propan-1-one and 1-(5-methyl-1,3-dioxan-5-yl)-2-(1,2,4-triazol-1-yl)-3-(4-ethylphenyl)-propan-1-ol.

3. A composition for regulating plant growth, comprising an effective amount of one or more compounds of the formula I as defined in claim 1 and a solid or liquid carrier.

4. A process for regulating plant growth which comprises: applying to the plants or their habitat an effective amount of one or more compounds of formula I as defined in claim 1.

5. A composition for regulating plant growth as defined in claim 3 which further includes one or more surfactants.

* * * * *

UNITED STATES PATENT AND TRADEMARK OFFICE
CERTIFICATE OF CORRECTION

PATENT NO. : 4,385,925
DATED : May 31, 1983
INVENTOR(S) : Costin Rentzea, Karl-Heinz Feuerherd, Bernd Zeeh and Johann Jung It is certified that error appears in the above-identified patent and that said Letters Patent is hereby corrected as shown below:

Claim 2, lines 33 and 34, cancel the following compound "1-(5-methyl-1,3-dioxan-5-yl)-2-(1,2,4-triazol-1-yl)-3-(4-chlorophenyl)-propane," and insert the following compound -- 1-(5-methyl-1,3-dioxan-5-yl)-2-(1,2,4-triazol-1-yl)-3-(4-chlorophenyl)-propan --.

Signed and Sealed this

Twenty-third Day of August 1983

[SEAL]

Attest:

GERALD J. MOSSINGHOFF

Attesting Officer    Commissioner of Patents and Trademarks